US006975108B2

(12) United States Patent
Bilik et al.

(10) Patent No.: US 6,975,108 B2
(45) Date of Patent: Dec. 13, 2005

(54) METHODS AND DEVICES FOR EDDY CURRENT PCB INSPECTION

(76) Inventors: Yuli Bilik, St. Wolfson 2/1, Holon 58344 (IL); Eytan Keydar, 4 Hatkuma St., Rehovot 76217 (IL); Vladimir Boroda, 23 MaDoneynu Bareth St., Ashdod 77642 (IL)

( * ) Notice: Subject to any disclaimer, the term of this patent is extended or adjusted under 35 U.S.C. 154(b) by 50 days.

(21) Appl. No.: 10/705,865

(22) Filed: Nov. 13, 2003

(65) Prior Publication Data

US 2005/0104585 A1 May 19, 2005

(51) Int. Cl.[7] .................. G01N 27/82; G01N 27/72; G01R 33/12; G01R 33/14
(52) U.S. Cl. .................. 324/237; 324/222; 324/228
(58) Field of Search .................. 324/222, 228, 324/229, 230, 231, 232, 233, 239, 240, 243, 324/241, 242, 237, 236

(56) References Cited

U.S. PATENT DOCUMENTS

| 3,528,004 | A | * | 9/1970 | Katabami ............. 324/236 |
| 3,619,771 | A | * | 11/1971 | Hentschel ............. 324/239 |
| 3,753,096 | A | * | 8/1973 | Wiers ............. 324/233 |
| 3,890,564 | A | * | 6/1975 | Watanabe et al. ............. 324/225 |
| 3,922,599 | A | * | 11/1975 | Steingroever et al. ....... 324/230 |
| 3,986,105 | A | * | 10/1976 | Nix et al. ............. 324/230 |
| 4,207,520 | A | * | 6/1980 | Flora et al. ............. 324/238 |
| 4,553,095 | A | * | 11/1985 | Schenk et al. ............. 324/230 |
| 5,006,788 | A | | 4/1991 | Goulette et al. |
| 5,182,513 | A | | 1/1993 | Young et al. |
| 5,237,271 | A | | 8/1993 | Hedengren |
| 5,333,052 | A | | 7/1994 | Finarov |
| 5,424,633 | A | | 6/1995 | Soiferman |
| 5,430,376 | A | * | 7/1995 | Viertl ............. 324/227 |
| 5,440,566 | A | | 8/1995 | Spence et al. |
| 2002/0027436 | A1 | | 3/2002 | Taylor |
| 2003/0016026 | A1 | | 1/2003 | Kawaike et al. |
| 2003/0025497 | A1 | * | 2/2003 | Collingwood et al. ...... 324/242 |

FOREIGN PATENT DOCUMENTS

| SU | AC191196 | 1/1967 |
| SU | AC789730 | 12/1980 |

* cited by examiner

*Primary Examiner*—Edward Lefkowitz
*Assistant Examiner*—Kenneth J. Whittington
(74) *Attorney, Agent, or Firm*—Mark M. Friedman (57) ABSTRACT

A non-contact printed circuit board (PCB) electromagnetic testing system comprises at least one high resolution transducer operative to induce multi-frequency, multi-amplitude eddy currents in a tested PCB, each such transducer including both a high frequency excitation coil that serves also as a sensing coil and a direct current (DC) bias coil operative to provide an optimal transducer operating regime; a multi-frequency generator for providing AC and DC bias signals to each transducer; and a control mechanism for driving the transducer. Optionally, the system further comprises an external ferrite concentrator that enhances a magnetic field flux focus and depth of focus on the inspected PCB. The multi-frequency, multi-amplitude methods enable three-dimensional mapping of various features in the PCB with both high sensitivity and high resolution in respective operating regimes.

15 Claims, 10 Drawing Sheets

Fig.3    3a- without "normalizing";    3b – with "normalizing".

$I_{F1} > I_{F2}$;    1-LF signals level of top layer;    2-LF signals level of lower layer.

METHODS AND DEVICES FOR EDDY CURRENT PCB INSPECTION

FIELD OF THE INVENTION

The present invention relates generally to printed circuit board. (PCB) inspection methods and systems, and more particularly to manual and automatic non-contact electromagnetic (EM) inspection devices, methods and systems used on unpopulated single layer or multilayer PCBs.

BACKGROUND OF THE INVENTION

Quality control is very important during the fabrication of a printed circuit board. Although etching processes are precisely prepared and controlled, some defects may appear on a PCB. Defects such as opens or shorts may immediately lead to rejection of the PCB, while micro-semi-cracks or filamentary shorts, poor cleanliness, or geometrical changes in the conducting paths may create hidden faults, which may deteriorate the functionality of the assembled PCB to the point of rendering it useless.

Existing methods for PCB inspection include various optical methods for PCB layer inspection, electrical methods used mainly for final PCB testing, X-ray and thermal methods. A main requirement for all of these methods is high resolution, considering the small width of modern PCB tracks, which starts at about 100 micron.

The most frequently used direct imaging optical methods are based either on visual recognition processes, or on laser methods that rely on fluorescent effects of the plastic substrate. A manual visual method is limited in performance, labor-intensive and prone to human fatigue. Both visual and laser methods have high optical resolution, but are limited in their ability to reveal narrow cracks or filament-type shorts and other invisible flaws, such as salt, residues left over from the etching process, or under-etching characterized by a series of random copper dots and partially conducting surfaces. The principle of detection in most optical systems is based on differences in reflectivity between the non-conducting substrate and the conductive materials (cooper, gold, etc.). As mentioned by Finarov in U.S. Pat. No. 5,333,052, an optical inspection system becomes ineffective, generating many false alarms when the conductive surfaces suffer from colorization due to metal oxidation (which changes color and reflectivity). Laser inspection systems use illumination of the inspected surface and comparison of the difference in fluorescence between the substrate and the conductors, to provide high contrast in the image of the two materials. However, laser-based optical inspection cannot be used to distinguish between two non-fluorescing materials, such as two metal layers, or to image a thin insulating film on a metal layer that does not fluoresce because of its composition or thinness.

Another well-know technique is electrical contact testing (ECT), mostly used for final PCB testing. In certain cases, ECT is also appropriate for PCB layer testing, especially for first article inspection. Conventional ECT techniques for automated PCB testing apply electrical signals through one set of test pins, and measure output signals through another set of test pins. ECT systems are of two main types: "flying probes" and "bed-of-nails". Both require tight mechanical contact between the test pins and the tested PCB and high mechanical tolerances, as indicated for example by Soiferman in U.S. Pat. No. 5,424,633. A "flying probes" technique is very slow and of low effectiveness. A "bed-of-nail" system for every PCB requires special and unique mechanical jigs with high mechanical precision. Along with the recent developments in high-density PCBs with extremely fine parts and wiring patterns, it has become difficult to correctly position test probes onto the areas to be inspected in the case of inspections using an in-circuit tester. Moreover, when test probes are positioned on a high density PCB, the circuit board might be damaged due to disconnections induced in the wiring pattern, as mentioned by Kawaike et al in U.S. patent application Ser. No. 10/198,739. Additional disadvantages of ECT include its incapability to localize the position of a defect, and its low ability to observe conducting path geometry violations.

X-ray technologies may also be used in some cases to inspect the quality of PCBs, mostly of assembled ones. These technologies require very expensive and complex equipment, also involving safety issues.

Other methods of PCB inspection are based on thermal imaging of the inspected surfaces, e.g. the method mentioned by Spence in U.S. Pat. No. 5,440,566. In general, thermal methods are characterized by low resolution and complex processing.

Non-contact electromagnetic systems and methods for PCB inspection are known. One such contacless testing system (CTS) is disclosed by Soiferman in U.S. Pat. No. 5,424,633. The inspected PCB is placed under an energizing plate connected to an alternating current (AC) signal, and an EM field is generated around the plate. The EM field penetrates through the inspected PCB workpiece, creating a so-called integrated electromagnetic image of the PCB patterns. A set of EM sensors is placed on the other side of the PCB, with an insulation layer placed between sensor and PCB surface. In a coordinate system in which the inspected plane is XY and the depth direction is Z, the EM field signal detected by a sensor represents a pattern of the inspected PCB at the particular XY coordinate where the sensor is located. The main limitation of this system is its low resolution and the impossibility to reveal defects in the Z (depth) direction. In other words, Soiferman's method cannot provide a high resolution 3-dimensional PCB pattern image. Daalmans, in German Patent No. DE19757575 describes an electromagnetic microscope with an eddy current (EC) measuring head, where the corresponding response signal is detected inductively or capacitively via the measuring head resonance circuits. The measuring head has a collection of small planar coils. The main limitation of Daalmans' method and system is the low inductivity of the coils, which requires the use of an excitation signal from a transmitter coil at very high frequencies. This means that the EC penetration depth is very small, and that it is impossible to detect any defects inside the subsurface region.

Goulette et. al. in U.S. Pat. No. 5,006,788 describe a similar method, where a current is applied to a PCB to be inspected in order to generate an electric or magnetic field distribution on the PCB, by connecting all conducting paths to an AC current source. This feature makes the method non-universal and labour-intensive.

Various types of eddy current probes and probe arrays are known. In general, every EC probe has coils wound on a ferromagnetic core, and placed within close proximity to the inspected surface. The ferromagnetic core is used to intensify an induced electromagnetic field flux. A drive coil is used to induce the magnetic field into inspected surface. A sense coil operates to receive current mutually induced by the resultant flux due to the eddy current flow. Any defect in the conducting surface will disrupt the flow of induced current. This disruption is detected by the sense coil and recognized as a defect.

Kawaike et al. above describe a system and method wherein eddy currents are generated on the PCB board to be inspected. Kawaike's detection method has low resolution for distinguishing between faulty and good patterns, and cannot determine the type of defect and its lateral localization in the PCB.

D. Kacprzak et al., in the 6th Int. Workshop on Electromagnetic Non-destructive Evaluation, 2000.6, (hereafter Kacprzak2000) disclose another type of eddy current sensor using a meander driving coil and an air solenoid pick-up coil as a sense coil. The pick-up coil measures a tangential component generated by eddy currents. Their technique is limited by the very small signal generated by the tangential component, which is very difficult to preserve in practice when high scanning velocities are used. Another limitation of the tangential component measurement is the substantial difficulty in inspecting a multilayer PCB. Their results are reported for double-sided boards and conductor widths larger than 200 micrometers, i.e. dimensions much larger than those used in the PCB industry, i.e. not applicable to modern PCBs manufacturing parameters.

In multilayer PCBs, the ability to separate between layers and between layer sides (see below) is important. It is also important to detect the lateral placement of a defect. The common approach in such a case is to use a multi-frequency driving technique, based on fact that the EC penetration depth is inversely proportional to the exciting electromagnetic field frequency. Bilik in USSR Author Certificate AC191196 and USSR Author Certificate AC789730, and Hedengren in U.S. Pat. No. 5,237,27 describe such methods, in which a multi-frequency AC signal is applied to an EC sensor for adjusting the range of penetration depth, thereby adjusting the flaw detection resolution and sensitivity. Another example of using a multi-frequency technique is disclosed by Young et al. in U.S. Pat. No. 5,182,513, in which multi-frequency driving allows the probe sensitivity to be tuned via a proper choice of drive frequencies, thus obtaining improved response concerning flaw detection. All methods mentioned above use multi-frequency driving to change the EC penetration depth in order to improve the data collection sensitivity. The main disadvantage of each of these methods is the requirement to use a wide range of driving frequencies to change the penetration depth.

The resolution of the sensor is also a very important parameter during PCB inspection. A modern PCB track pitch has a spacing of 75–150 micrometer. Therefore, the resolution of the testing sensor becomes very critical. Prior art eddy current probes provide a focus of the magnetic field flux that is commensurable with the diameter of the exciting coil. Some prior art uses an external focusing fixture around the sensor. Taylor in U.S. patent application Ser. No. 09/416,868 proposes a metallic shield disposed around the coil and operative to focus the eddy current field within the structure. Such a fixture focuses the field only within the shield and not inside the inspected structure.

There is therefore a widely recognized need for, and it would be highly advantageous to have an electomagnetic non-contact PCB and PCB layer testing method that does not suffer from the disadvantages mentioned above.

OBJECTS OF THE INVENTION

A first object of the present invention is to reveal PCB manufacturing defects by providing an eddy current sensor with a ferromagnetic core that gives maximal magnetic field sharp focus (gradient) in the small gap between a transducer and an inspected PCB layer.

Another object of the invention is to achieve a sharp focus of the EM field flux on the PCB surface to be inspected, by placing an external magnetic field concentrator on the opposite side of the PCB to improve defects detection and eddy current image resolution.

Yet another object of the invention is to provide a maximal transducer EM field flux focus by choosing an appropriate value of magnetic permeability of the transducer's ferrite core using a combination of two coils wound along the core, a DC bias coil and AC excitation coil.

Yet another object of the invention is to provide a minimum magnetic dissipation flow in the section of the transducer far from the inspected object, by providing a ferrite ring placed above a defense ring. Alternatively, and for the same purpose, the transducer coil may be coated by ferromagnetic varnish replacing the ferrite ring.

Yet another object of the invention is to provide an EC method that allows to separate each side of a PCB layer during layer inspection, in order to locate a defect placement (in the X-Y-Z coordinates) and define its character, and to build a 3-dimensional EC image of the PCB.

A final object of the invention is to provide a system using the transducer and method above for non-contact inspection of unpopulated PCB, that is to detect micro defects such as conductor micro cracks and opens, filamentary shorts between adjacent conductors, etching defects, etc.

SUMMARY OF THE INVENTION

According to the present invention there is provided a high resolution transducer for non-contact electromagnetic testing, comprising: an insulator body; a ferrite core inserted in the insulator body and having a tapered end, the core characterized by a magnetic permeability and operative to provide a focused magnetic field flux; a high frequency coil disposed around the core operative to induce multi-frequency, multi-amplitude EM fields excitations in the core, the excitations further inducing corresponding eddy currents in a tested element; and a direct current mechanism operative to optimize the magnetic permeability of the core, correlated with a transducer operating regime, whereby the transducer enables non-contact multi-frequency, multi-amplitude testing of single and multi-layered printed circuit boards that reveals layer defects with high three-dimensional resolution.

According to the present invention there is provided a transducer for non-contact electromagnetic testing of a printed circuit board comprising: an excitation mechanism operative to induce multi-frequency, multi-amplitude eddy currents in the PCB, the eddy currents providing three-dimensional PCB data; and a direct current based transducer regime setting mechanism operative to provide at least two different operating regimes of the transducer, thereby improving a parameter of the transducer.

According to the present invention there is provided a non-contact printed circuit board electromagnetic testing system comprising: at least one transducer operative to induce multi-frequency, multi-amplitude eddy currents in a tested PCB, each transducer including a direct current mechanism operative to provide an optimal transducer operating regime, the induced eddy currents resulting in a frequency dependent electromagnetic field with a normal component that carries PCB output information; a multi-frequency generator for providing AC and DC signals to each transducer; and an acquisition and processing mechanism for processing the PCB output information.

According to the present invention there is provided a non-contact electromagnetic method for printed circuit board inspection comprising the steps of: providing at least one transducer operative to apply multi-frequency, multi-amplitude excitation EM fields to the PCB board, the excitation EM fields inducing corresponding eddy currents in the PCB board layers, each transducer further characterized by having an elongated ferrite core ending in a tapered end, and a direct current mechanism operative to set at least one transducer operating regime; using the DC mechanism to set a transducer operating regime; applying the multi-frequency, multi-amplitude EM fields to obtain corresponding eddy currents, each of the eddy currents providing a separate frequency sense signal; and processing the sense signals, thereby obtaining high resolution, three-dimensional data revealing defects and other faults in the PCB.

The present invention provides inspection systems and methods using eddy currents for accurate contactless measurement of flaws in single or multilayer PCBs, particularly deviations from standard patterns that include the width of paths, their cracks and all visible and invisible flaws. The invention discloses a transducer that has high resolution and which is especially useful in the testing of small conductive details, e.g. narrow PCB tracks.

Eddy current non-destructive testing has a long history and many known applications such as investigations of large metal structures, plane wings, etc. Although this technique is well-known, its application for PCB inspection is non-obvious and requires development of special types of high resolution eddy current testing (ECT) sensors and methods of testing.

The present invention discloses a simple and inexpensive EC transducer for non-contact PCB inspection with a resolution level of 75–150 micrometers, especially suitable for modern PCBs. The transducer has a ferrite core with a magnetic field concentrator in the form of a tapered, preferably truncated conical end ending in a rather pointed tip. A sharp focus of the EM field is achieved also with the assistance of a DC induced magnetic bias regime of the ferrite core. The transducer's exciting HF coil is supplied with a small HF current to create a weak HF field of approximately 10–15 millioersted in the gap between its pointed tip and a PCB surface. The HF coil serves also as a sensing coil that can distinguish small variations of the coupled impedance due to eddy currents. To decrease the divergence of the EM field flux inside the PCB, an external ferromagnetic concentrator that promotes the formation of a sharp focus and depth of focus of the EM field is positioned on the same axis as the transducer on the opposite side of the PCB.

In order to increase the sensitivity, a parametric modulation of a high frequency generator with the necessary sensitivity is used, the modulation applied by very small changes of the linear reactive component (transducer), which is connected into its tuned circuit. This allows reception of transducer coupled impedance signal changes that are of the order of a fraction of a percent. The coupled impedance is proportional to the amount of the conducting material under the sensor and other parameters known from an impedance diagram.

The parameters of the signals received by the transducer while scanning over PCB paths depend also on the relationship between the path geometry and the transducer diameter, as well as on the path quality and the transducer supply current and frequency values.

The present invention also discloses an EC method for obtaining data from separate, individual layers in a multi-layer PCB. This method enables one to build a 3-D eddy current PCB image, and to process and analyze every PCB layer; thus defining defects more precisely.

Finally, the present invention discloses an EC system for non-contact, real time PCB inspection, based on the EC transducer and the method of PCB layers separation mentioned above. The system preferably includes two arrays of EC transducers that simultaneously and synchronously scan two respective PCBs, one known as a "good" workpiece and the other known as the "inspected" one. The system allows to inspect the PCB very quickly, even without a computerized aided manufacturing (CAM) database of PCB layer images (Gerber files), which are provided in general by a layout engineer.

BRIEF DESCRIPTION OF THE DRAWINGS

The invention is herein described, by way of example only, with reference to the accompanying drawings, wherein:

FIG. 7 shows in (a) a preferred embodiment of a local inductance transducer according to the present invention, and in (b) and (c) the procedure for choosing an operating point for, respectively, large and small HF amplitudes (respectively for a thick and a thin PCB).

DESCRIPTION OF THE PREFERRED EMBODIMENTS

The present invention provides eddy current devices, systems and methods used to inspect single and multilayer PCBs, and to receive information from every PCB layer separately. The systems and methods include further data processing of the sensed information. The invention discloses a novel transducer having a ferrite core with preferably a sharp conical, pointed end, which provides a high EM field gradient in the small gap, typically 0.5–0.2 mm, between the transducer and the inspected PCB surface. In a preferred embodiment, a sharp focus of the electromagnetic field is obtained on the PCB surface by placing an external electromagnetic field concentrator on the opposite side of the PCB. A transducer with maximal resolution is obtained by choosing a correct value of a permanent magnetic bias for the transducer's ferrite core, using a DC bias. The system of the present invention ensures minimum magnetic dissipation flow in the section of the transducer far from the inspected object, by placing a ferrite ring above a protective ring around the core. The transducer and its elements are described in detail in FIG. 7.

The inspection method disclosed herein uses scanning the surface of a single-layer or multilayer PCB with the transducer, which provides a highly focused EM field flux when it is very close to the surface region. One innovative feature in a preferred embodiment of the present system and method is that there is one "common" transducer used to inspect all the layers of the multilayer PCB. The common transducer is supplied with two or more currents of different amplitudes and different frequencies. This represents a novel "multi-frequency multi-amplitude approach" to EC PCB inspection. The preferable selection is a set with a number of frequencies double the number of the PCB layers, because every layer has a conductive pattern on two sides. Hereafter, a "side" of a PCB layer refers to one of its two substantially parallel planes. Each frequency is selected to insure enough EM field penetration through the entire PCB or selected layers of the PCB to reach a required side, with low attenuation inside the PCB or the selected layers respectively. The use of multi-frequencies allows simultaneous processing of signals from individual sides through frequency discrimination.

In a particular case, the carrier of each frequency is a sinusoidal signal of a definite amplitude. The amplitudes are selected in such a way as to enable a different depth of penetration of the EM field into the PCB. For example, assume that a signal of frequency $F_1$ and a current amplitude $I_1$ creates an EM field of a strength that induces perceptible (to the transducer) eddy currents only in the upper side of the first PCB layer. Similarly, assume that a signal of the frequency $F_2$ and current amplitude $I_2$ induces perceptible eddy currents only in both (upper and lower) sides (called henceforth respectively "side 1" and "side 2") of the first PCB layer, and that a signal of frequency $F_3$ and current amplitude $I_3$ induces perceptible eddy currents only in both sides 1 and 2 of the first PCB layer and in side 1 of the second PCB layer, etc. In other words, the first signal "probes" side 1 of layer #1 only, the second signal probes both sides of the same layer #1, the third signal probes the formerly mentioned two sides of layer #1 plus side 1 of layer #2, etc. It is clear that a received signal that corresponds to the coupled impedance signal of frequency $F_1$ will contain data corresponding to an EC image of side 1 of layer #1 only, and a received signal of frequency $F_2$ will contain data corresponding to a superposition of EC images from sides 1 and 2 of layer #1. It is also clear that the coupled impedance and its signal of side 1 of layer #1 received on frequency $F_2$ will be greater than the same signal received on frequency $F_1$. It can be said that, approximately, their ratio will be equal to the known ratio between the excited EC amplitudes. It is therefore possible to normalize the signal amplitude of side 1 of layer #1 received on frequency $F_1$ ("component 1") to the signal amplitude of side 1 of layer #1 received on frequency $F_2$ ("component 2") by multiplying component 1 by the mentioned ratio. Now, subtracting the result of the multiplication from the entire signal received on frequency $F_2$, we obtain the EC component of side 2 of layer #1. In a similar manner a separation of each side of every PCB layer can be performed.

The present method and system can change the absolute EC depth of penetration not so much by changing the frequencies of the exciting fields (which is known in applications to metals), but by changing the strength of these fields. The frequencies used may be quite close to each other (in single "common transducer" embodiments) or even equal (in the embodiments using several transducers, each supplied by different currents and with the same frequency).

The eddy current transducer of the present invention creates a normal (perpendicular to the PCB surface) EM field and is therefore referred to as a "normal field component" EC transducer. This derives from the fact that the axis of the transducer, with its "pencil" shape core, is perpendicular to the PCB plane, therefore receiving signals only from the normal component of the 3-dimensional EM field formed by the eddy currents. This contrasts with the "tangential" transducer of Kacprzak2000, which analyzes a tangential field component. As mentioned, the normal transducer of the present invention has a sharp focus (high EM field gradient) of a high frequency magnetic field flux in the space between its end and the tested surface. The diameter of the transducer "inspection spot" is of the same order or less than that of modern PCB tracks, i.e. 75–150 $\mu$m. Except for the main (excitation and sensing) coil, supplied by an alternating HF current, there is an additional coil, supplied by a DC current, which serves to bias the core's magnetic material, thereby affecting the core magnetic permeability. Alternatively, in a separate embodiment, the transducer may have a single coil that receives both AC HF and DC inputs, the same coil thus serving for both DC bias of the operating regime (see below), for multi-frequency, multi-amplitude HF excitation of eddy currents, and for sensing the EC induced normal EM field component. When the magnetic permeability $\mu$ is equal to its maximal value $\mu_{max}$, the magnetic field flux has the best focus, leading to the best resolution. Therefore, the operating point condition for free air is chosen on the (positive) right slope of the $\mu$=f(H) graph (see e.g. FIG. 7b), where $H_{HF}$=(1.5–1.7) $H_{max}$ in air, and $\mu < \mu_{max}$. In this case, a PCB track presence will drive the graph to the $\mu = \mu_{max}$ point thereby improving the resolution. The use of a small diameter ferrite (ferromagnetic) rod, and the utilization of a conical-end technique, guaranties a sharp focus of interest and enables working with current track widths technology. Both resolution and field penetration depth may be increased by the addition of a ferrite concentrator under the inspected PCB. The concentrator maybe in the form of a flat ferrite layer, a razor sharp line of ferrite, or a sharp pointed ferrite rod. All these measures provide a transducer with a sharp magnetic field focus.

The exciting current and frequency of the transducer are chosen such as to enable it to receive information from several layers (and from each layer's two sides) of the multilayer PCB. As a result, a data stream is created and processed into an electromagnetic image of the inspected layers. This image contains data of the coupled impedance inserted by eddy currents for each of the points on the scanning transducer's trajectory, which corresponds to the conductive nature of the inspected points, resulting, when processed appropriately, in a clear differentiation between conducting tracks, such as copper, and an insulating substrate, such as FR4. It is also possible to differentiate between a nominally conducting material and a fractured, partly conducting material, or a partly conducting contaminated substrate. A typical processing algorithm may compare the resultant image with a nominal pattern that is the original target of the production process, or may take a KGI (Known Good Item) as a basis for fault determination. The KGI can be achieved statistically from the inspection of a whole batch. The difference between the good reference image and the inspected image will lead to fault identification in the conductance pattern, un-influenced by other apearances of the inspected sample (e.g colorization).

Figure 1:
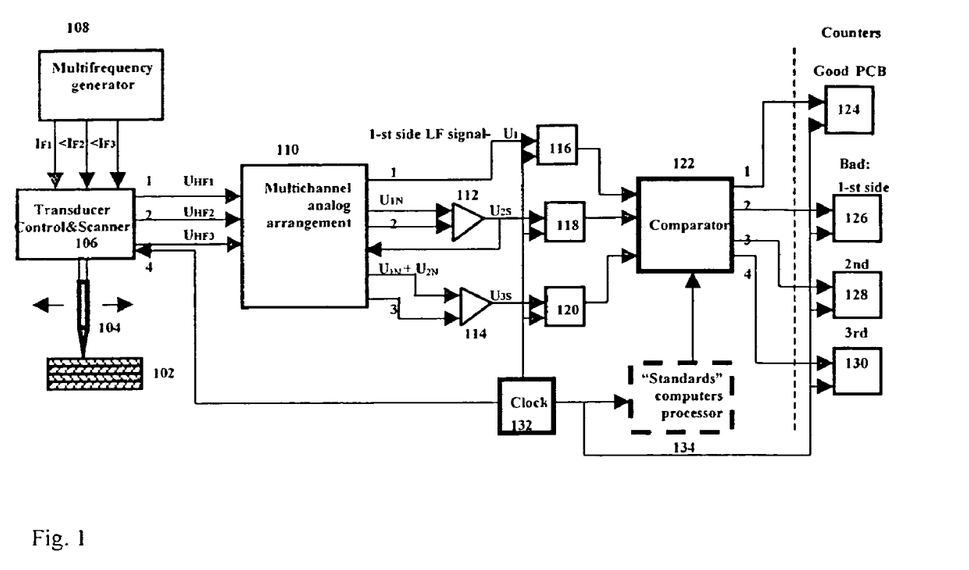
FIG. 1 shows a block-diagram of a single common transducer, parallel signal processing EC system for multi-layer PCB inspection according to the present invention.

Referring now to the figures, FIG. 1 shows a block-diagram of a single common transducer, parallel signal processing EC system for multilayer PCB inspection according to the present invention. The EC system implements a parallel method of processing the signals of all layers of a PCB 102 simultaneously ("parallel signals processing"), and of receiving information separately from each side of every layer of PCB 102, using a single innovative transducer 104, which is described in more detail in FIG. 7a. A transducer Control & Scanner circuitry 106 is used to facilitate the driving of transducer 104 by a multi-frequency generator 108. Generator 108 provides several AC currents of different frequencies $I_F$, which number is double the number of the PCB layers. The exciting current amplitudes are preferably choosen as follows:

$$I_{F1} < I_{F2} < I_{F3} \tag{1}$$

in inverse proportion to the exponential law of EC depth of penetration in metals. That is, the amplitudes are chosen to receive approximately the same transducer coupled EM field (EMF) from different layers:

$$E_{F1} = E_{F2} = E_{F3} \tag{2}$$

where $E_{Fn}$ is the EMF coupled from a layer/side correlated with a respective frequency $F_n$. For a particular example of two layers, the absolute EC depth of penetration $D_{F3}$ of current $I_{F3}$ is chosen equal to the thickness of two layers, $D_{F2}$ for current $I_{F2}$ is chosen equal to the thickness of one layer, and $D_{F1}$ for current $I_{F1}$ is chosen equal to a thickness of less than that of one layer.

FIG. 1 shows a specific case of inspection of three sides only in order to simplify the circuits drawing. Multi-frequency generator 108 may be implemented in several embodiments, for example by a plurality of independent generators, by a harmonics generator, or by two generators combined with a mixer and used to create a set of combination frequencies. That is, one may use signals of independent generators and combine them by superposition, use one generator and apply its output to a nonlinear element to receive a set of harmonics, or use two generators and multiply their signals in order to receive a set of combination frequencies.

Transducer 104 is controlled by transducer Control & Scanner 106 and may scan the PCB surface lineraly (line by line), in a rotating movement or in another manner, exciting eddy currents in the conducting surfaces. The coupled impedances produce by the eddy current EMFs create a parametric modulation of three carrier frequencies $U_{HF1}$, $U_{HF2}$, $U_{HF3}$, which appear on outputs 1, 2, 3 of Control & Scanner 106. A multi-channel analog arrangement 110 divides high frequency signals $U_{HF1}$, $U_{HF2}$, $U_{HF3}$ according to their frequencies. Amplification, detection and filtration in arrangement 110 result in low frequency (LF) signals $U_1$, $U_2$, $U_3$ which are fed to inputs of two subtractors 112 and 114. $U_1$, $U_2$, $U_3$ are an envelope and represent a coupled impedance inserted by eddy currents from every side of layer 1. $U_1$ corresponds to the upper side eddy current image, $U_{2S}$ corresponds to the second (lower) side, and $U_{3S}$ to the third (upper side of layer 2). $U_1$ is an envelope of $U_{F1}$, $U_2$ is an envelope of $U_{F2}$, and $U_3$ is an envelope of $U_{F3}$. $U_{1N}$ is a $U_1$ signal normalized for $U_2$, and in the same manner $U_{1N}+U_{2N}$ is a summed signal of $U_1$ and $U_2$ normalized for $U_3$. The results of the subtraction, $U_1$, $U_{2S}$ and $U_{3S}$ are then digitized by A/D digitizers 116, 118 and 120 and compared by a comparator 122 with standard images, stored in a storage medium, preferably a computer 134.

In case of mismatch between a digitized U image and a standard image, an "alarm" signal ("2", "3", "4") is generated and entered on block counters 126, 128, 130, indicating a "bad" PCB. If an alarm signal is absent ("1"), a "good" PCB counter 124 is activated. All processes mentioned above are synchronized by a clock 132.

Figure 2:
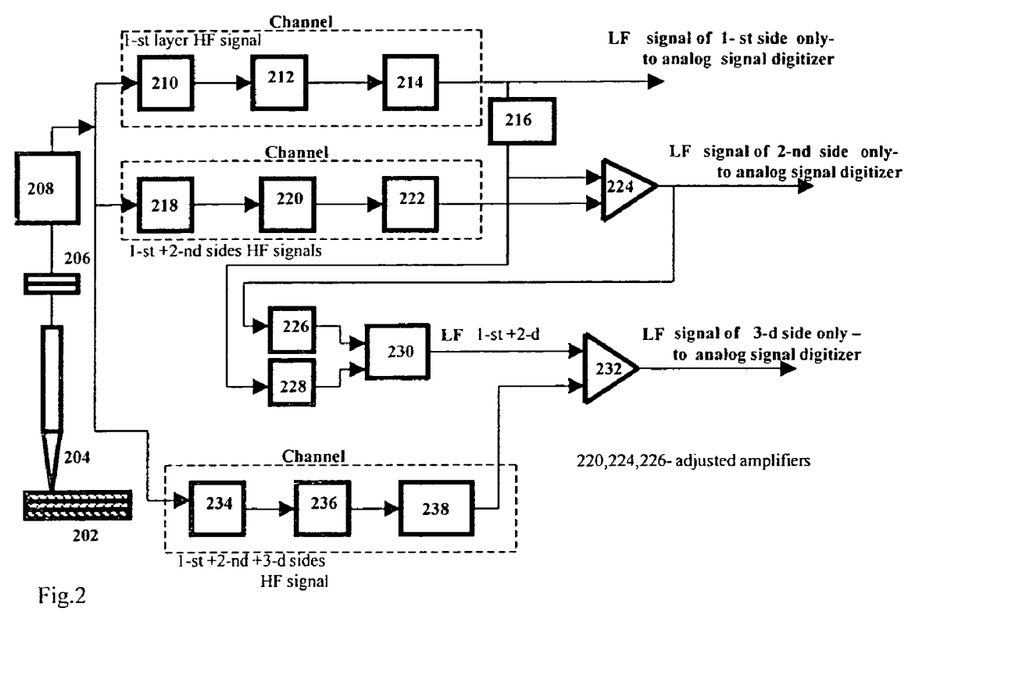
FIG. 2 shows details of a multichannel analog arrangement of FIG. 1.

FIG. 2 shows details of multichannel analog arrangement 110 of FIG. 1. A PCB 202 is scanned by a common transducer 204. A generator 208 supplies current to transducer 204 through a non-contact collector 206. Its main frequency and the second and third harmonics are extracted respectively by selective amplifiers 234, 218 and 210. We receive LF signals on the outputs of channels # 1, 2, 3, with amplitudes proportional to the coupled impedance inserted by the eddy currents from respectively layer sides 1, (1+2) and (1+2+3). Each channel has elements for each HF carrier: a demodulator 210 for $F_1$, 218 for $F_2$ and 234 for $F_3$, an amplifier 212 for $F_1$, 220 for $F_2$ and 236 for $F_3$, and a lowpass filter 214 for $U_1$, 222 for $U_2$ and 238 for $U_3$.

Figure 3:
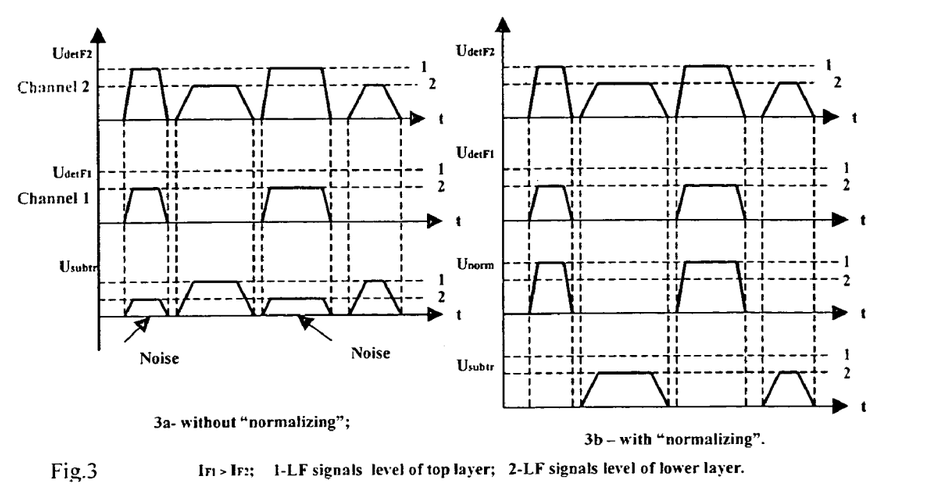
FIG. 3 illustrates a method of separating signals from two adjacent layers using a so-called "normalizing" procedure.

Amplifiers 216 and 228 are used to adjust the signal from side 1 for side 2, and from side 1 for side 3 respectively. Amplifier 226 is used to adjust the signal from side 2 for side 3. A buffer 230 matches the amplifiers 226, 228 to an input of subtractor 232. The LF signal of side 1 is fed directly from the channel #1 output to its respective digitizer. The LF signals of sides 2 and 3 separately are similarly fed from outputs of subtractors 224, 232 to their respective digitizers. Thus, information from each side is received simultaneously and continuously. FIG. 3 demonstrates a method for separating signals from two adjacent sides using a so-called "normalizing" procedure. Assume that the EC penetration depth $D_1$ of frequency $F_1$ is less than $D_2$ of frequency $F_2$. In a particular case, they may be equal:

$$D_2 = 2 * D_1 \tag{3}$$

In a more general case the above ratio may be found experimentally during pretesting calibration.

In FIG. 3, graph [a] shows signals without "normalization". In channel #2 (top), we can see two kinds of signals: a larger amplitude one from the top side of layer 1 and a smaller amplitude one from the second, bottom side of layer 1. In channel #1 we can see only signals from the top side of layer 1. In general, their amplitude is not equal to that of the similar (first layer top side) signal in channel #2. Consequently, after subtraction we will receive a "clutter" signal as a result of top side amplitude non-equality in the two channels, in addition to signals from the bottom side. To overcome this deficiency, it is necessary to normalize the signals' amplitudes of same sides in different channels, which are connected to a common subtractor, as demonstrated in graph [b] on FIG. 3. To get $U_{norm}$ (i.e. normalize $U_{detF1}$ to $U_{detF2}$) we need to multiply $U_{detF1}$ by the ratio $D_2/D_1$.

Figure 4:
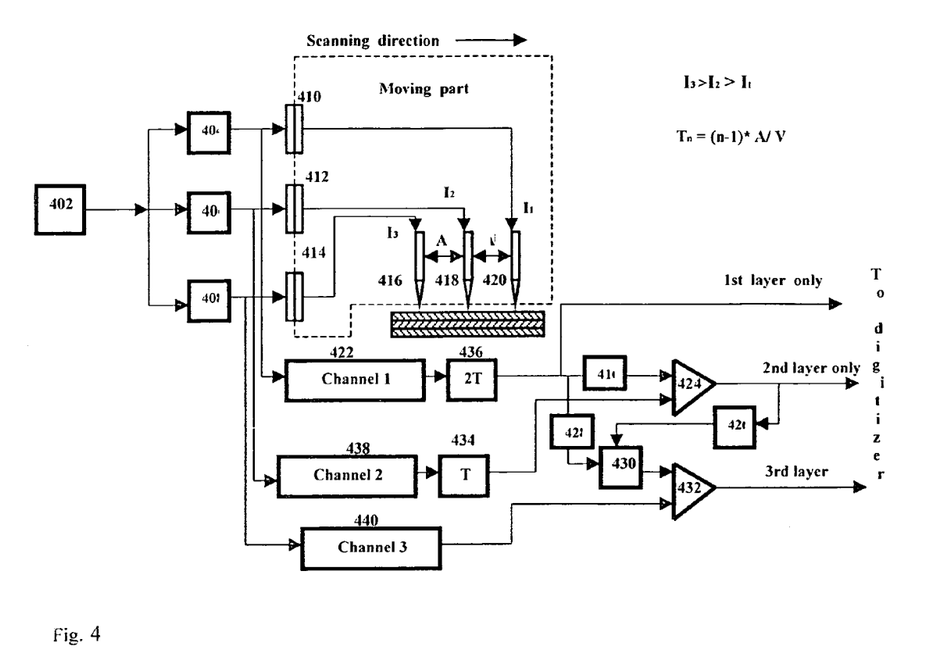
FIG. 4 shows a block-diagram of the parallel signals processing method using three separate transducers.

FIG. 4 shows a block-diagram of the parallel signals processing method using separate transducers, which allows to set their operating regime independently. By "independent setting" we mean that it is possible to set for every transducer an appropriate DC bias value to provide maximal resolution, see discussion re. FIG. 7 below. A generator 402 provides transducers 416, 418, and 420 with same frequency but different amplitude HF currents $I_1 < I_2 < I_3$, through buffer amplifiers 404, 406, 408 and non-contact collectors 410, 412, 414. These transducers are placed at a constant spacing A apart, above the PCB to be inspected, in one line that coincides with the scanning direction. Preferably, A=1.0–2.0 mm. The generator HF frequency, modulated by coupled impedances of one, two or three PCB sides, is fed to inputs of three analog channels 422, 438, and 440. The channels outputs provide LF signals that correspond to changes in coupled impedances along the scanning trajectory. Another difference between this method and the one embodied in FIG. 2 lies in the presence of time-delay arrangements 434, 436, which are used to align in time signals of two channels 1 and 2 with respect to the signal of channel 3. In general, the time delay $T_n$ equals $$T_n=(n-1)*A/V \quad (4)$$

where n is the number of the transducer in the scanning direction, and V is the constant scanning speed.

Figure 5:
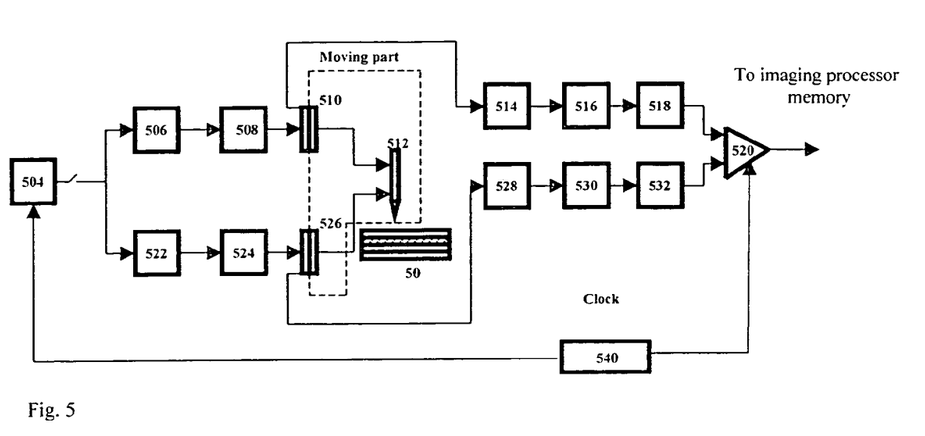
FIG. 5 shows a block-diagram for a series signal processing EC PCB inspection system according to the present invention.
Figure 6:
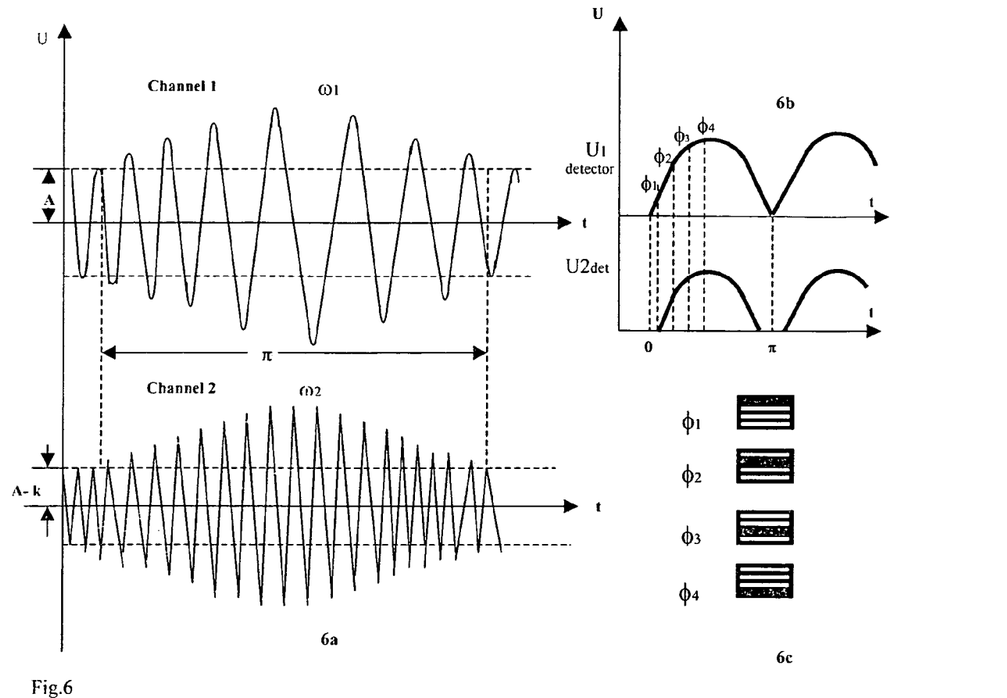
FIG. 6 illustrates graphically the method for series signal processing using the system of FIG. 5.

FIG. 5 shows a block-diagram for a series signals processing system according to the present invention. FIG. 6 illustrates graphically the method for series signal processing using the system of FIG. 5. In contrast with the parallel signal processing method, the series one uses just two frequencies. This method provides scanning not only in the XY plane, but simultaneously also in the Z-axis direction. The set-up requires only two channels and one common transducer. A modulator 504 produces a unipolar low frequency periodic voltage, for example pulses after a sinusoidal voltage rectification (before filtration) as shown in FIG. 6b, or a sawtooth-type voltage. This voltage modulates two HF generators 506 and 522 of different frequencies (see FIG. 6a) and different current amplitudes. Their voltages are fed through buffer amplifiers 508, 524 and non-contact collectors 510, 526 to a common transducer 512, which scans a PCB 502. Due to the difference in the EM fields strength, and partly due to the different frequencies, there is difference in the EC absolute depths of penetration $D_1$ and $D_2$. This difference is chosen to be equal to the thickness of one layer:

$$D_1-D_2=1 \text{ layer thickness}=\text{const} \quad (5)$$

After processing the amplitude modulated (AM) HF signals by amplifiers 514, 528, AM detectors 516, 530 and LF filters 518, 532, two LF signals $U_1$ and $U_2$ appear on the input of a subtractor 520. A difference LF signal $\Delta U$ on the subtractor output given by:

$$\Delta U=|U_1|-|U_2| \quad (6)$$

always carries information about the increment of coupled impedance for one side, the depth of which depends on the time-dependent difference between $D_1(t)$ and $D_2(t)$ at every moment. Considering the modulation amplitude changes, we receive as a result a scan on the depth, see also FIG. 6c. Φs represent different phases of the modulating voltage, as well as the particular layer numbers inspected (shaded layers). The output of subtractor 520 is stored in the imaging processor memory, and after scanning the entirel PCB surface, the image of each layer is reconstructed and processed for defect detection.

Figure 7A:
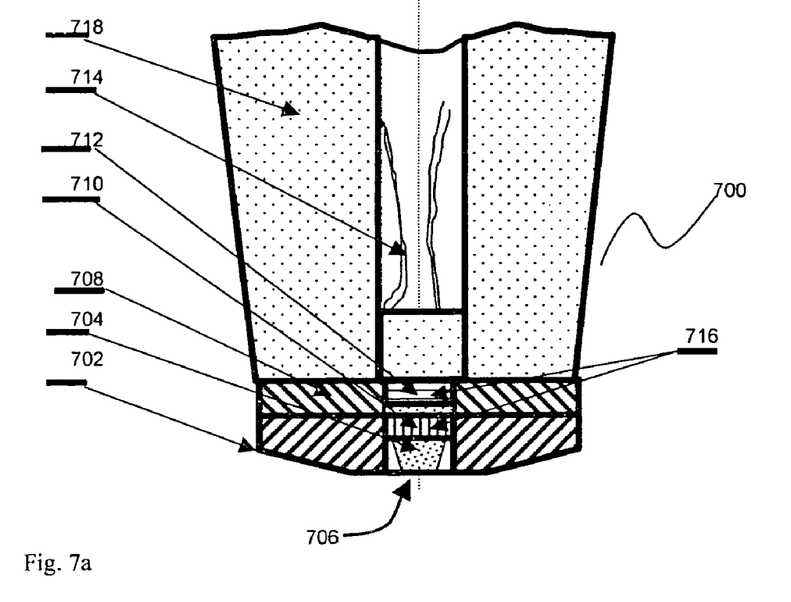

FIG. 7 shows in (a) a preferred embodiment of a local inductance transducer 700 according to the present invention, which is supplied with high frequency AC and DC currents. The transducer further comprises a protective ring 702 that covers the conical end and protects it from any mechanical damages. Ring 702 may be made from nonconductive material (e.g. hard plastic or ceramic or even a hard stone like ruby) or from a metal with high electrical conductivity like cooper or silver. A metallic ring has the additional property of shielding the magnetic field flux, thus improving the transducer focus. The transducer comprises a ferrite core 704, which has the general shape of a rod with a truncated end 706, a ferrite ring 708, an HF coil 710, a optional separate DC bias coil 712, wire leads 714 that lead to Control&Scanner unit 106 in FIG. 1, and an insulator body 718. Core 704 has preferably a simple geometry cross section, e.g. circular, hexagonal or rectangular, the tapered end accordingly being conical, or in the shape of a trucated pyramid with a hexagonal or rectangular base. The tapered end, as in a "pencil" may end in a rather sharp point. In core 704, a truncated conical end is preferable because: 1) it is the simplest natural geometrical form that gives symmetrical concentration of the magnetic field flux, creating a round magnetic pixel/spot, and 2) it is technologically simpler to process a ferrite cylindrical rod to get a sharp conical end with a pointed tip. However, and as mentioned, the rod may be processed to get the shape of a truncated pyramid, in which case the rectangular or square ferrite end point of the truncated pyramid will provide an almost rectangular or square magnetic pixel/spot on the inspected surface.

Optionally, the function of DC coil 712 may be incorporated in HF coil 710, removing the need for a separate DC coil. Further optionally and alternatively, either or both coils 710 and 712 may be covered by a ferromagnetic varnish 716.

A main innovative feature of transducer 700 is the separate DC magnetic bias, which is created by DC bias coil 712 (or by a DC bias function incorporated in HF coil 710). The separate DC control facilitates the change of the core magnetic permeability $\mu$, enabling two operating regimes, one of a sharp (maximal) field focus, and the other of a high (maximal) sensitivity, when the transducer is placed above a conducting surface, particulary above the PCB tracks. In other words, the DC bias coil acts as an operating regime setting mechanism. These two operating regimes are explained by FIGS. 7b and 7c. The first regime is intended for inspection of a thick PCB, having more than one layer, i.e. more than two conducting sides.

Figure 7B:
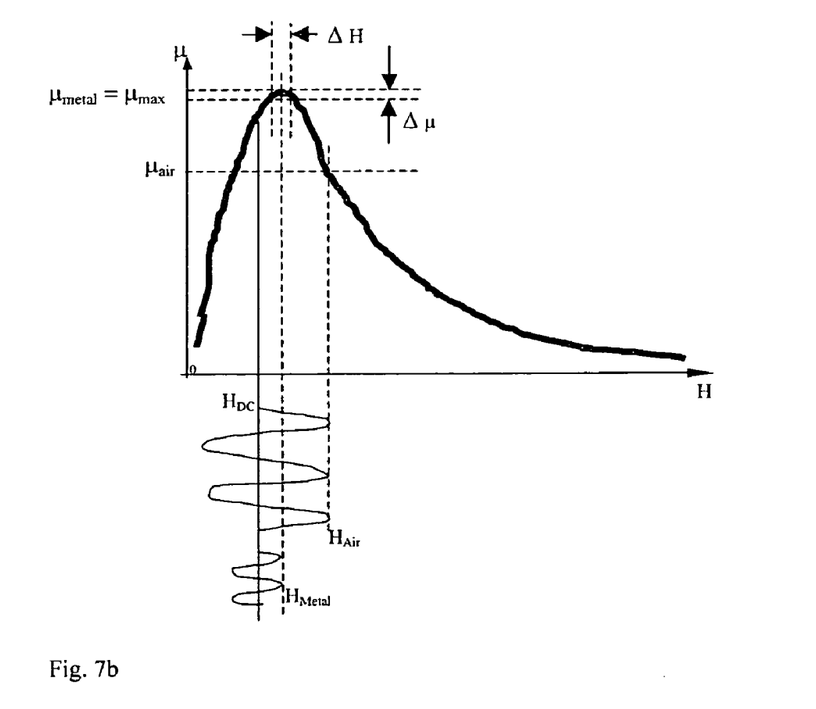

FIG. 7b shows the regime of maximal field focus, which is reached when the magnetic permeability of the ferrite core is maximal. In order to arrive to $\mu_{max}$ when the transducer is positioned over ("meets") a conducting surface, we set a DC bias and supply an AC exciting signal in such a way that a superposition of DC and AC fields reaches a maximum on the right slope of curve $\mu=f(H)$, i.e. at point $\mu_{air}$. When the transducer meets a conductive surface, eddy currents are induced below the transducer and their opposite magnetic field creates a resultant magnetic field that corresponds to $\mu_{max}$, i.e. the point of maximal permeability. That means a best focus but low sensitivity to very small defects, because small changes in $\Delta H$ lead to small changes in $\Delta \mu$.

Figure 7C:
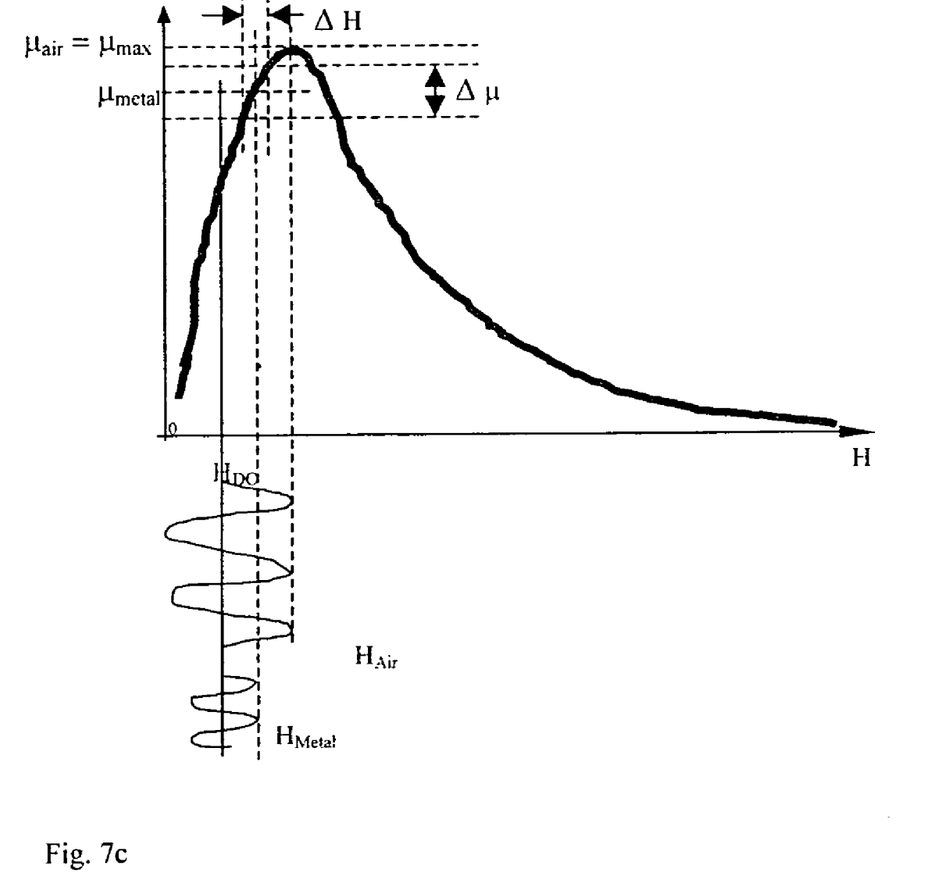

FIG. 7c shows the regime of maximal sensitivity, intended for inspection of a PCB that has no more than one layer, i.e. just two sides. A maximal sensitivity is reached when small changes in $\Delta H$ lead to large changes in $\Delta \mu$. In this case, the transducer becomes very sensitive to very small defects. This is obtained when we set a DC bias and supply an AC excitation signal in such a way that a superposition of DC and AC fields reaches a maximum on the peak of curve $\mu=f(H)$ at point $\mu_{max}$. When the transducer meets a conductive surface, the eddy currents are induced below the transducer and their opposite magnetic field creates a resultant magnetic field that corresponds to $\mu_{metal}$ on the left slope of curve $\mu=f(H)$. Now, small changes in H due to small defects result in large changes in $\mu$, i.e. in a high sensitivity of the transducer.

Figure 8:
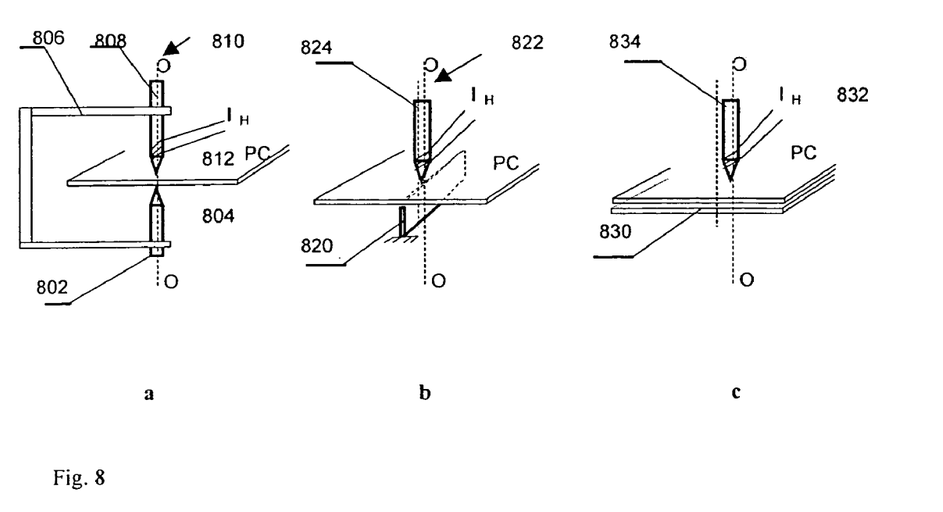
FIG. 8 shows various embodiments of a parametric transducer with an external EM field concentrator according to the present invention.

The inspection scanning mode can be realized in two ways: from one side of the PCB, or from two sides simultaneously. One side scanning involves one transducer, and in some embodiments involves a novel, external ferrite concentrator which preferably resembles a pointed transducer (FIG. 8a) or has a linear, razor type shape (FIG. 8b). Two-side scanning involves two transducers on both sides of a PCB, scanning simultaneously. When the tracks density is small (e.g. for h>3d, where "h" is the distance between two narrows tracks and "d" is the diameter of the "inspection spot"), it is possible to use the one-side scanning mode for the simultaneous inspection of two or more layers in a multilayer PCB.

FIG. 8a shows an exemplary design of an external magnetic (e.g. ferrite) pointed concentrator 802 with a tapered end 804, connected by a rigid mechanical connection 806 to a transducer 808, both placed on a common axis 810 on opposite sides of an inspected PCB 812. Concentrator 802 is used to increase the concentration of the magnetic field and to provide a sharper focus to the inspected point on the PCB. FIG. 8b shows a design with a static linear (blade or razor shape) magnetic concentrator 820. A transducer 824 and concentrator 820 share an axis 822. $I_{HF}$ indicates the HF current supplied to the transducer, while $V_{scan}$ in FIG. 8b shows the direction of scanning, defined by the direction of the external linear concentrator. As mentioned, the importance of a concentrator lies in it enhancing the sharp focus for inspecting and scanning multilayer PCBs. A multilayer PCB thickness is very small, (typically 1.4–1.6 mm), therefore allowing such an external concentrator to significantly affect the focus. Yet alternatively, a flat ferrite plate (not shown) may serve as a concentrator, while also serving as a support plate for the PCB. Note that such use of an external concentrator in EC testing of PCBs is not known to be practiced in the art.

Figure 9:
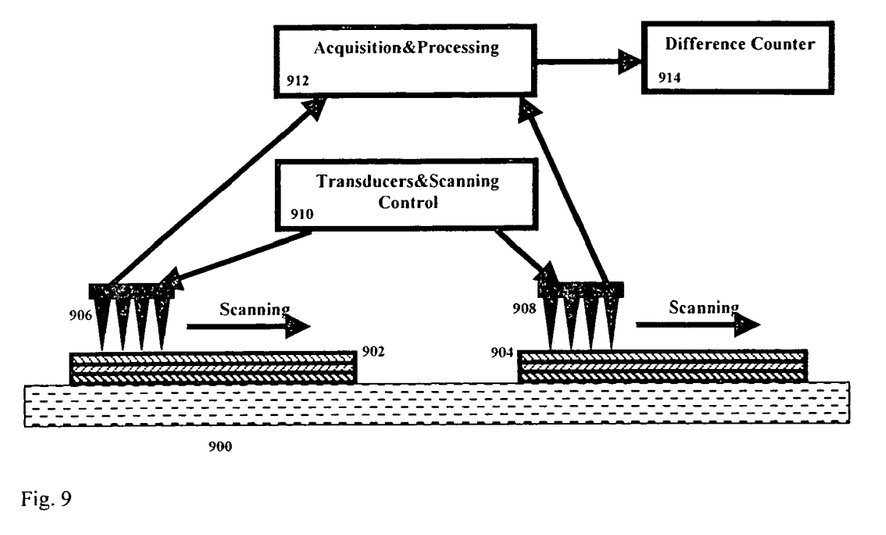
FIG. 9 shows a system for non-contact real time PCB inspection in a "comparison" mode.

FIG. 9 shows a system for non-contact real time PCB inspection in a "comparison" mode. The system comprises two arrays of eddy current transducers 906 and 908 that simultaneously and synchronously scan two PCB patterns assumed to be identical. A first PCB 902 is known as a "good" workpiece. A second PCB 904 is the inspected PCB. Both PCBs are placed on an inspection platform 900, and rigidly fixed on it. Preferably, as an initial condition, both transducer arrays should be placed over the coordinates of both PCBs. A transducer and scanning control unit 910 drives both arrays and controls their scanning over the PCBs. An acquisition and processing unit 912 recives the signals from both arrays, processes them, and builts eddy current images of both inspected PCBs. A difference counter 914 receives two images, and compares them, counting the differences between them. Such a system allows to inspect a PCB very quickly, even if a CAM database does not exist. In general, for layer inspection, such a system may inspect in real time all PCB identical patterns placed on the inspected PCB layer, to qualify them and their displacement on the layer surface, and to reject bad samples which have defects out of tolerances.

In summary, the present invention discloses a novel transducer, system and method for non-contact electromagnetic testing of PCBs. In simple terms, using one or more transducers as described above, we first set a DC bias to obtain an optimal operation regime for each transducer. We then apply a set (double the number of layers in a multilayer PCB) of alternating high frequency currents with different frequencies and amplitudes, to each transducer through an HF coil. Optionally, we may add a concentrator below the PCB to focus the inspection point. The eddy currents created due to each separate HF current create in return an EMF with a normal component that induces an impedance coupled into the HF coil (which acts also as a sense coil). We thus have one induced (coupled) impedance for each exciting HF current. If more than one HF current is applied, the coupled impedance is parametrically modulated, resulting in a number of output signals equal to the number of the original HF excitation currents. These output signals are processed, and the result of this processing yield the "imaging." The signals may be processed in parallel or in series.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described with respect to a limited number of embodiments, it will be appreciated that many variations, modifications and other applications of the invention may be made. Those skilled in the art will appreciate that the invention can be embodied by other forms and ways, without losing the scope of the invention. The embodiments described herein should be considered as illustrative and not restrictive. For example, the invention has been described with reference to analog processes and analyses. It would be obvious to one skilled in the art that these processes and analyses may be equally well performed using appropriate digital, i.e. software and DSP technology, provided the digitization of the analog data is of high enough resolution.

What is claimed is:

1. A high resolution transducer for non-contact electromagnetic testing, comprising:
   a. an insulator body;
   b. a ferrite core inserted in said insulator body and having a tapered end, said core characterized by a magnetic permeability and operative to provide a focused magnetic field flux;
   c. a high frequency (HF) coil disposed around said core operative to induce multi-frequency, multi-amplitude electromagnetic (EM) field excitations in said core, said excitations further inducing corresponding eddy currents in a tested element; and
   d. a direct current (DC) mechanism operative to optimize said magnetic permeability of said core, correlated with a transducer operating regime,
   whereby the transducer enables non-contact multi-frequency, multi-amplitude testing of single-layered and multi-layered printed circuit boards that reveals layer defects with high three-dimensional resolution.

2. The transducer of claim 1, wherein said DC mechanism includes a DC coil disposed around said core.

3. The transducer of claim 1, wherein said DC mechanism includes means to supply a DC bias to said HF coil.

4. The transducer of claim 1, further comprising a ferrite ring surrounding said core, said ferrite ring operative to prevent magnetic flow dissipation.

5. The transducer of claim 1, wherein said operating regime is characterized by a maximal core magnetic permeability that provides a high transducer resolution.

6. The transducer of claim 1, wherein said transducer operating regime is characterized by a high transducer sensitivity.

7. The transducer of claim 1, further comprising a protective ring located on said core around said tapered end, said protective ring used to protect said tapered end from damage.

8. The transducer of claim 7, wherein said protective ring is a metallic ring operative to shield and further focus said magnetic field flux.

9. The transducer of claim 2, wherein said tapered end is conical, ending in a substantially sharp point.

10. The transducer of claim 2, further comprising a ferromagnetic varnish coating on at least one of said coils.

11. A transducer for non-contact electromagnetic testing of a printed circuit board (PCB) comprising:
   a. an excitation mechanism operative to induce multi-frequency, multi-amplitude eddy currents in the PCB, said eddy currents providing three-dimensional PCB data; and
   b. a direct current (DC) based transducer regime setting mechanism operative to provide at least two different operating regimes of the transducer, thereby improving a parameter of the transducer, wherein the transducer includes a rod-type ferrite core characterized by a magnetic permeability correlated with said operating regimes, said core having a tapered end facing said PCB, wherein said excitation mechanism includes a high frequency (HF) coil disposed around said core operative to induce multi-frequency, multi-amplitude EM fields excitations in said core, said excitations further inducing corresponding eddy currents in the PCB, and wherein said regime setting mechanism includes a DC bias mechanism operative to change said magnetic permeability of said core.

12. The transducer of claim 11, wherein said DC bias mechanism includes a DC coil disposed around said core.

13. The transducer of claim 12, wherein said DC bias mechanism includes means to supply a DC bias to said HF coil.

14. A non-contact printed circuit board (PCB) electromagnetic testing system comprising:
   a. at least one transducer operative to induce multi-frequency, multi-amplitude eddy currents in a tested PCB, each said at least one transducer including:
      i. an elongated ferrite core with a tapered end for providing a sharp focus to an inspection point having a depth of focus on said PCB, said core having a length axis substantially perpendicular to said PCB and facing with said tapered end a first side of said PCB
      ii. a direct current (DC) mechanism operative to provide an optimal transducer operating regime, said induced eddy currents resulting in a frequency dependent electromagnetic field with a normal component that carries PCB output information, and
      iii. an external electromagnetic concentrator positioned in close proximity on an opposite side of said PCB and substantially aligned with said at least one transducer length axis, said concentrator operative to increase the concentration of a magnetic field formed by said core and improve said focus and said depth of focus, wherein said external concentrator is substantially similar in shape to said core;
   b. a multi-frequency generator for providing AC and DC signals to said at least one transducer; and
   c. an acquisition and processing mechanism for processing said PCB output information.

15. A non-contact electromagnetic method for printed circuit board (PCB) inspection comprising the steps of:
   a. providing a transducer operative to apply multi-frequency, multi-amplitude excitation EM fields to the PCB board, said excitation EM fields inducing corresponding eddy currents in the PCB board layers, said transducer further characterized by having an elongated ferrite core ending in a tapered end and a direct current (DC) mechanism operative to set at least one transducer operating regime,
   b. using said DC mechanism to set one said transducer operating regime;
   c. applying said multi-frequency, multi-amplitude EM fields to obtain said corresponding eddy currents, each of said eddy currents providing a separate frequency sense signal, wherein said step of applying said multi-frequency, multi-amplitude EM fields includes applying simultaneously two modulated carriers of different amplitudes and frequencies and obtaining said sense signals in the form of one difference signal; and
   d. processing said sense signals, thereby obtaining high resolution, three-dimensional data revealing defects and other faults in the PCB, wherein said step of processing said sense signals includes processing said difference signal to obtain depth resolved information that is compared with a virtual or a physical PCB standard.

* * * * *